United States Patent
Lee et al.

(10) Patent No.: US 9,687,423 B2
(45) Date of Patent: Jun. 27, 2017

(54) METHOD FOR PREPARING NANOEMULSION

(71) Applicant: COSMAX, INC., Hwaseong-si (KR)

(72) Inventors: Jun Bae Lee, Yongin-si (KR); Chun Ho Park, Yongin-si (KR); Moung Seok Yoon, Daejeon (KR); Hee Chang Ryoo, Seoul (KR)

(73) Assignee: COSMAX, INC., Gyeonggi-Do (KR)

( * ) Notice: Subject to any disclaimer, the term of this patent is extended or adjusted under 35 U.S.C. 154(b) by 0 days.

(21) Appl. No.: 14/913,519

(22) PCT Filed: Aug. 12, 2014

(86) PCT No.: PCT/KR2014/007490
§ 371 (c)(1),
(2) Date: Feb. 22, 2016

(87) PCT Pub. No.: WO2015/026095
PCT Pub. Date: Feb. 26, 2015

(65) Prior Publication Data
US 2016/0199269 A1    Jul. 14, 2016

(30) Foreign Application Priority Data

Aug. 23, 2013    (KR) .................. 10-2013-0100283

(51) Int. Cl.
*A61K 8/06*    (2006.01)
*A61K 8/42*    (2006.01)
(Continued)

(52) U.S. Cl.
CPC .................. *A61K 8/06* (2013.01); *A61K 8/34* (2013.01); *A61K 8/345* (2013.01); *A61K 8/42* (2013.01);
(Continued)

(58) Field of Classification Search
None
See application file for complete search history.

(56) References Cited

U.S. PATENT DOCUMENTS

2007/0275021 A1    11/2007    Lee et al.
2010/0286102 A1*   11/2010    Vielhaber ................ A61K 8/34
                                                             514/171

FOREIGN PATENT DOCUMENTS

JP    2009261929    11/2009
KR    20030021709    3/2003
(Continued)

OTHER PUBLICATIONS

Flockhart, et al, Nanoemulsions derived from lanolin show promising drug delivery properties, J. Pharm. Pharmacol., 1998, p. 141.
(Continued)

*Primary Examiner* — Bethany Barham
*Assistant Examiner* — Barbara Frazier
(74) *Attorney, Agent, or Firm* — Cantor Colburn LLP

(57) ABSTRACT

Provided is a method for preparing a nanoemulsion, including mixing an oil phase part (A) containing a ceramide or derivative thereof, cholesterol, non-ionic surfactant, phospholipid and a polyol, a perfume part (B) containing a perfume ingredient, non-ionic surfactant and an alcohol, and an aqueous phase part (C) containing the other water-soluble active ingredients. When a nanoemulsion is obtained by the method, it is possible to reduce processing time and cost since a non-ionic surfactant is used without a high-pressure emulsification process, and the obtained nanoemulsion is more stable against a change in temperature than the other solubilized formulations.

4 Claims, 3 Drawing Sheets
(3 of 3 Drawing Sheet(s) Filed in Color)

(51) Int. Cl.
- *A61K 8/92* (2006.01)
- *A61K 8/34* (2006.01)
- *A61K 8/55* (2006.01)
- *A61K 8/63* (2006.01)
- *A61Q 13/00* (2006.01)
- *A61Q 19/00* (2006.01)

(52) U.S. Cl.
CPC ............... *A61K 8/553* (2013.01); *A61K 8/63* (2013.01); *A61K 8/922* (2013.01); *A61Q 13/00* (2013.01); *A61Q 19/00* (2013.01); *A61K 2800/21* (2013.01)

(56) References Cited

FOREIGN PATENT DOCUMENTS

| | | |
|---|---|---|
| KR | 20050026778 | 3/2005 |
| KR | 20080086231 | 9/2008 |
| KR | 20090018953 | 2/2009 |
| KR | 20090132670 | 12/2009 |
| KR | 20100071013 | 6/2010 |
| KR | 20100100202 | 9/2010 |
| KR | 20110076068 | 7/2011 |

OTHER PUBLICATIONS

Elias, et al., Mammalian Epidermal Barrier Layer Lipids: Composition and Influence on Structure, The Journal of Investigative Dermatology, 1977, pp. 535-546.

Flockhart, et al, Nanoemulsions derived from lanolin show promising drug delivery properties, J. Pharm. Pharmacol., 1998, p. 141.

International Search Report—PCT/KR2014/007490 dated Nov. 26, 2014.

* cited by examiner

METHOD FOR PREPARING NANOEMULSION

TECHNICAL FIELD

The present disclosure relates to a method for preparing a nanoemulsion. More particularly, the present disclosure relates to a method for preparing a nanoemulsion, including mixing an oil phase part (A) containing a ceramide or derivative thereof, cholesterol, non-ionic surfactant, phospholipid and a polyol, a perfume part (B) containing a perfume ingredient, non-ionic surfactant and an alcohol, and an aqueous phase part (C) containing the other water-soluble active ingredients.

BACKGROUND ART

Skin barriers resisting against infiltration of external harmful materials into the skin are largely present on the strateum corneum of the skin epidermis. Such a strateum corneum functions to protect the human body from physical damages caused by external factors and from chemicals, and interrupts evaporation of moisture in the human body to prevent skin dryness. Active studies have been conducted about lipid ingredients in the structure of the strateum corneum. Elias and coworkers have reported that the lamellar structure formed of the lipid ingredients in the stratum corneum is the origin of such a skin barrier function (J. Invest. Dermatol. 69: 535-546, 1977). In addition, although there is a difference depending on the experimental method and the position of a skin tissue, it is known that intercellular lipids substantially include about 50% of ceramides, 20-25% of cholesterol, 20-25% of free fatty acids, about 10% of cholesterol ester, 1-2% of cholesterol sulfate and a small amount of phospholipids.

To apply such a skin barrier function to cosmetics, many studies have been conducted to simulate the skin barrier function and various formulations, such as a liquid crystal emulsion, have been developed. The main purpose of such formulations is stable incorporation of intercellular lipids that are main ingredients providing such a skin barrier function, and many studies have been conducted about ceramides, cholesterols and phospholipids. Particularly, since it was known that ceramides and cholesterols are not only main ingredients of intercellular lipids that are main ingredients of skin barriers but also strong moisturizing ingredients, stabilization thereof has been studied intensively. However, when using them in conventional emulsion formulations, they undergo gelling with time. Thus, in most cosmetic formulations, they are used in a very small amount, or are subjected to a separate pretreatment process using a high-pressure emulsification system, such as a microfluidizer, to form a stabilized material before they are applied to cosmetics. However, such high-pressure emulsification requires a special system and complicated process and shows undesirably low cost-efficiency. To overcome the problems, many studies have been conducted to solubilize ceramides or to convert ceramides into nanoliposomes through high-pressure emulsification.

For example, Korean Patent Publication No. 10-2005-0026778 discloses 'Cosmetic Composition for Alleviating Skin Irritation Including Nanoliposomes of Intercellular Lipid Ingredients' and Korean Patent Publication No. 10-2011-0076068 discloses 'Vesicles Including Self-Emulsifiable Nanoliposomes/Multilayer Liquid Crystals, and Preparation and Use Thereof'. In both patent documents, nanoliposomes are obtained by using high-pressure emulsification in order to stabilize intercellular lipid ingredients including ceramides, cholesterols and phospholipids. However, the methods according to both patent documents use a special system (i.e., high-pressure emulsification system), and thus require additional cost and time undesirably. In addition, Korean Patent Publication No. 10-2010-0100202 discloses a stable solubilized formulation containing micelles of intercellular lipid ingredients having a size of 1-200 nm and the solubilized formulation does not require high-pressure emulsification. However, the obtained stable solubilized formulation is limited to a formulation having a selected size of approximately 1-200 nm. In addition, according to the studies of the present inventors, it has been found that such a formulation causes a problem related with stability, including precipitation of intercellular lipid ingredients during the storage at 45° C. and 50° C., and during the thawing after the refrigeration at −20° C. It is known that a solubilized formulation obtained by dissolving sparingly soluble/insoluble materials, such as perfume or oil, having hydrophobic property and hardly water-soluble property into water by using a material (solubilizing agent) having amphiphilic property (i.e., both hydrophilicity and hydrophobicity) has one phase having a thermodynamically stable and uniform spherical structure. Since such a solubilized formulation is thermodynamically stable, it is very stable regardless of mixing methods and orders, when the conditions, such as temperature or composition, are compatible. However, because highly hydrophobic materials, such as ceramides or cholesterols, to be solubilized in the above-mentioned manner allow solubilization only in the inner part of the solubilizing agent (i.e., in the core spaces), there are not sufficient spaces for solubilization. Therefore, highly hydrophobic materials to be solubilized require a significantly larger amount of solubilizing agent as compared to the solubilization process of perfume or oil. In this case, some problems, including a sticky feeling of use and irritation to the human body, may occur undesirably.

Under these circumstances, the inventors of the present disclosure conducted intensive studies to overcome the above-mentioned problems. After the studies, we have found that it is necessary to minimize mass transfer through the interface in order to improve the stability of a nanoemulsion containing a large amount of intercellular lipid ingredients. Based on this, we have found a novel method for preparing a nanoemulsion containing a large amount of intercellular lipid ingredients. When a nanoemulsion is obtained by the novel method, it is possible to reduce processing time and cost since a non-ionic surfactant is used without a high-pressure emulsification process, and the obtained nanoemulsion is more stable against a change in temperature as compared to the other solubilized formulations. The present disclosure is based on this finding.

DISCLOSURE

Technical Problem

A technical problem to be solved by the present disclosure is to provide a method for preparing a nanoemulsion that uses a non-ionic surfactant without a need for a high-pressure emulsification process to reduce the processing time and cost, and provides a nanoemulsion more stable against a change in temperature as compared to the other solubilized formulations.

Another technical problem to be solved by the present disclosure is to provide a cosmetic composition including the nanoemulsion obtained by the above-mentioned method.

Technical Solution

In one general aspect, there is provided a method for preparing a nanoemulsion, including the steps of:

a) mixing, warming and dissolving a ceramide or derivative thereof, cholesterol, non-ionic surfactant, phospholipid and a polyol to obtain an oil phase part (A);

b) dissolving a perfume ingredient and non-ionic surfactant into an alcohol to obtain a perfume part (B);

c) dispersing and dissolving a polyol and water-soluble active ingredient into water to obtain an aqueous phase part (C);

d) adding the oil phase part (A) to the aqueous phase part (C) and further adding the perfume part (B) to the aqueous phase part (C), followed by agitation, to obtain a reaction mixture; and e) filtering the reaction mixture of step d) through a filtering paper or filtering cloth.

As used herein, the term 'emulsion' means a liquid-liquid dispersion system including a first liquid phase and at least one liquid phase immiscible with the first liquid phase and dispersed in the first liquid phase, and generally has a particle size of several micrometers to several tens of micrometers. The emulsion having the above-defined range of particle sizes is thermodynamically unstable and finally causes separation through various paths, such as flocculation, sedimentation, creaming, Ostwald ripening and coalescence. In addition, although there is a slight difference according to research workers and documents, an emulsion whose dispersion phase particles have an average diameter of 20-500 nm is referred to as 'nanoemulsion' (Flockhart, I. R. et al., J. Pharm. Pharmacol., 50 (Supplement) 1998, 141). Since such a nanoemulsion has a small particle size, it is less affected by the gravity and allows the Brownian motion among the particles, and thus is more stable against sedimentation, creaming or the like, as compared to a general emulsion. The nanoemulsion is also an emulsion and cannot be said to be thermodynamically stable. However, it can be said that a nanoemulsion has improved kinetic stability as compared to a general emulsion by virtue of the Brownian motion.

In addition, unlike a microemulsion or general emulsion, a nanoemulsion allows dilution with an aqueous phase with no change in particle size (Colloid Surface A 2004; 251: 53-8).

A typical surfactant that may be used for preparing such a nanoemulsion includes lecithin, an intercellular phospholipid. Lecithin undergoes self-emulsification when mixed with a sufficient amount of aqueous medium to form a double-layer or multilayer lamellar while producing nano-sized particles. When using high-pressure emulsification during the self-emulsification of lecithin, it is possible to obtain a very fine nanoemulsion having a size of several nanometers to several tens of nanometers.

However, a high-pressure emulsification method requires a special system and complicated process and shows undesirably low cost-efficiency. In addition, when forming a stable solubilized formulation containing micelles having a size of 1-200 nm while not using high-pressure emulsification, the solubilized formulation is limited to one having a selected size of approximately 1-200 nm and is not stable against a change in temperature. Moreover, the materials to be solubilized can be solubilized only in the inner part of a solubilizing agent (i.e., core spaces) and highly hydrophobic materials to be solubilized require a very large amount of solubilizing agent. When using a large amount of solubilizing agent, some problems, such as a sticky feeling of use and irritation to the human body, may occur undesirably.

Under these circumstances, according to the present disclosure, it has been found that when using a non-ionic surfactant for preparing a nanoemulsion including intercellular lipid ingredients, such as ceramides and cholesterols, without using high-pressure emulsification, it is possible to form a stable nanoemulsion including a large amount of intercellular lipid ingredients and to significantly improve the stability of a solubilized formulation. The present disclosure is based on this finding.

In order to improve the stability of a nanoemulsion including a large amount of intercellular lipid ingredients, mass transfer through the interface should be minimized. In general, a glycol is added instead of a preservative during the preparation of a nanoemulsion. Such a preservative (glycol) attacks the nanoemulsion, which, in turn, causes the intercellular lipids present in the liposomes to come out of the liposomes, resulting in degradation of stability. Thus, minimization of mass transfer means preventing the materials present in the liposomes from coming out to the exterior. Therefore, it is possible to improve the stability of a nanoemulsion by minimizing such mass transfer.

In the method for preparing a nanoemulsion according to the present disclosure, a non-ionic surfactant is also dissolved into an alcohol together with a perfume ingredient to obtain a perfume part separately. When the perfume part is not prepared separately but is incorporated to and mixed with an oil phase part, the perfume ingredient is present in the nanoliposomes. Herein, while the nanoliposomes are attacked by the co-added preservative (glycol), the perfume ingredient present in the liposomes may come out of the liposomes. After the perfume ingredient comes out of the liposomes, the formulation becomes turbid with time and has decreased stability. On the contrary, when using the perfume part separately from a non-ionic surfactant, the perfume part is solubilized by the non-ionic surfactant and is present in the aqueous phase in a stable form. Thus, it is possible to stabilize the nanoemulsion from the attack of a preservative such as a glycol.

In the method for preparing a nanoemulsion according to the present disclosure, the aqueous phase part may further include a water-soluble active ingredient, in addition to a polyol and water. The water-soluble active ingredient is any material that may be dissolved into water to form an aqueous phase part, and particular examples thereof include anti-wrinkle functioning materials, whitening materials and natural extract.

The anti-wrinkle material may include adenosine, and the whitening material may include albutin, niacin amide, or the like. In addition, the natural extract may include natural vegetable, animal or mineral extract extracted from aloe, green tea, citrus, gingko leaves, or the like. The water-soluble active ingredient is not limited to the above-mentioned examples.

In the method for preparing a nanoemulsion according to the present disclosure, when the oil phase part (inner part, dispersion phase) is introduced to and mixed with the aqueous phase part (outer phase, continuous phase) in step d), a nanoemulsion including particles having a size of 100-200 nm is formed. In addition, as described above with reference to the perfume part (B), the method for preparing a nanoemulsion according to the related art includes introducing perfume to an oil phase part, which, in turn, is added to the aqueous phase part to form a nanoemulsion. In this case, the perfume is present in the inner part of the nanoemulsion. However, the perfume present in the inner part of particles (inner phase) moves toward the aqueous phase part (outer phase) under the condition of high-temperature storage. Then, the nanoemulsion may become partially turbid (haze phenomenon) and causes degradation of stability. However, according to the present disclosure, when perfume is preliminarily mixed with an alcohol and non-ionic surfactant to form a perfume part and then the perfume part is introduced to the aqueous phase part at room temperature, the perfume is not present in the inner part but is solubilized so that it may be present in the aqueous phase in a stable form. Thus, even under the condition of high-temperature storage, no haze phenomenon occurs and the nanoemulsion may be present in a stable form. In other words, perfume is not introduced to the oil phase portion but is solubilized and then added to the aqueous phase portion so that the stability of the nanoemulsion may be improved under the condition of high-temperature storage. In this manner, it is possible to obtain a stable nanoemulsion in step d).

In the present disclosure, the non-ionic surfactant may be a combination of phospholipid with hydrogenated castor oil, octyldodeceth or Choleth. Preferably, there may be used a combination of hydrogenated castor oil-5, 7, 10, 20, 30, 40, 50, 60, 80 or 100, octyldodeceth-5, 10, 16, 20 or 25, or Choleth-5, 10, 15, 20, 24 or 30 with phospholipid.

Each of the numbers written with the non-ionic surfactants represents the number of polyethylene glycol (PEG) groups. As the number of PEG increases, hydrophilicity increases. In the same context, as the number of PEG increases, hydrophilic lipophilic balance (HLB) increases.

According to the following test examples of the present disclosure, when using phospholipid alone or using a single type of non-ionic surfactant without phospholipid (Examples 1-4), stability decreases under the conditions of high-temperature and refrigeration. On the contrary, when using a combination of phospholipid with a non-ionic surfactant (Examples 5 and 6), stability is improved as compared to the use of a single type of non-ionic surfactant. Moreover, when using a combination of phospholipid with Coleth-20 (Example 7), high stability is obtained at all tested temperatures. As a result, it can be seen that use of phospholipid or a non-ionic surfactant alone allows solubilization but causes degradation of stability, while a combination of phospholipid with a non-ionic surfactant allows solubilization and improves stability (Test Example 1).

In the present disclosure, the polyol may be at least one selected from the group consisting of propylene glycol, dipropylene glycol, 1,3-butylene glycol, pentylene glycol and 1,2-hexanediol. The polyol may be used in an amount of 0.1-10 wt % based on the total weight of emulsion.

In addition, the non-ionic surfactant used in step a) is the same as the non-ionic surfactant used in step b).

Particularly, the non-ionic surfactant used in step a) may be any one of hydrogenated castor oil-5, 7, 10, 20, 30, 40, 50, 60, 80 and 100, octyldodeceth-5, 10, 16, 20 and 25, and Choleth-5, 10, 15, 20, 24 and 30, and the non-ionic surfactant used in step b) is the same as the non-ionic surfactant used in step a).

In the present disclosure, the perfume ingredient may be oil used as perfume, perfume or a mixture thereof.

According to the present disclosure, the perfume ingredient is an oil-soluble ingredient that may be included in the micelle structures formed in the emulsion. The perfume does not refer to only a flavor-emitting material but includes perfume or a substitute thereof known in the field of cosmetics. Preferably, the perfume may be oil used as perfume, perfume or a mixture, and particular examples thereof include at least one selected from the group consisting of ester-based synthetic oil, silicon oil, such as dimethicone and cyclomethicone oil, animal and vegetable oil such as jojoba oil and squalene, synthetic perfume and natural perfume. In addition to the above, there may be used a material known to be cosmetically applicable and sparingly soluble.

In another aspect, there is provided a cosmetic composition including the nanoemulsion obtained by the above-described method.

According to the following test examples, it is shown from the skin safety test using each of the formulations obtained from Example 7 that each formulation causes skin irritation to a level less than 1, suggesting that it is little irritative. As a result, it can be seen that the cosmetic composition including the nanoemulsion obtained by the method disclosed herein is safe when applied to the skin (Test Example 2).

In the present disclosure, the cosmetic composition including the nanoemulsion obtained by the method disclosed herein may be provided in any conventional form known in the art. Particular examples of such forms include a solution, suspension, emulsion, paste, gel, cream, lotion, powder, soap, oil, powder foundation, emulsion foundation, wax foundation, spray or the like, but are not limited thereto. More particularly, the cosmetic composition may be provided in the form of skin, lotion, skin softener, nourishing skin, nourishing cream, massage cream, essence, eye cream, cleansing cream, cleansing foam, cleansing water, pack, spray or powder.

When the composition is provided in the form of paste, cream or gel, carrier ingredients that may be used include animal oil, vegetable oil, wax, paraffin, starch, tragacanth, cellulose derivatives, polyethylene glycol, silicon, bentonite, silica, talc or zinc oxide.

When the composition is provided in the form of powder or spray, carrier ingredients that may be used include lactose, talc, silica, aluminum hydroxide, calcium silicate or polyamide powder. Particularly, in the case of spray, a propellant, such as chlorofluorohydrocarbon, propane/butane or dimethyl ether, may be used additionally.

When the composition is provided in the form of a solution or emulsion, carrier ingredients that may be used include a solvent, solubilizing agent or emulsifier, and particular examples thereof include water, ethanol, isopropanol, ethyl carbonate, ethyl acetate, benzyl alcohol, benzyl benzoate, propylene glycol, 1,3-butylglycol oil, glycerol fatty acid ester, polyethylene glycol or sorbitan fatty acid ester.

In addition, when the composition is provided in the form of a suspension, carrier ingredients that may be used include a liquid diluent such as water, ethanol or propylene glycol, a suspending agent such as ethoxylated isostearyl alcohol, polyoxyethylene sorbitol ester or polyoxyethylene sorbitan ester, microcrystalline cellulose, aluminum metahydroxide, bentonite, agar or tragacanth.

Advantageous Effects

According to the embodiments of the present disclosure, intercellular lipid ingredients are stabilized by using the nanoemulsion obtained by a simple process using phospholipid and a non-ionic surfactant without high-pressure emulsification. In this manner, it is possible to reduce the processing time and cost as compared to the conventional high-pressure emulsification process. It is also possible to improve the stability of intercellular lipid ingredients at high temperature and under refrigeration as compared to the other known solubilized formulations.

DESCRIPTION OF DRAWINGS

The patent or application file contains at least one drawing executed in color. Copies of this patent or patent application publication with color drawing(s) will be provided by the Office upon request and payment of the necessary fee.

BEST MODE

Figure 1:
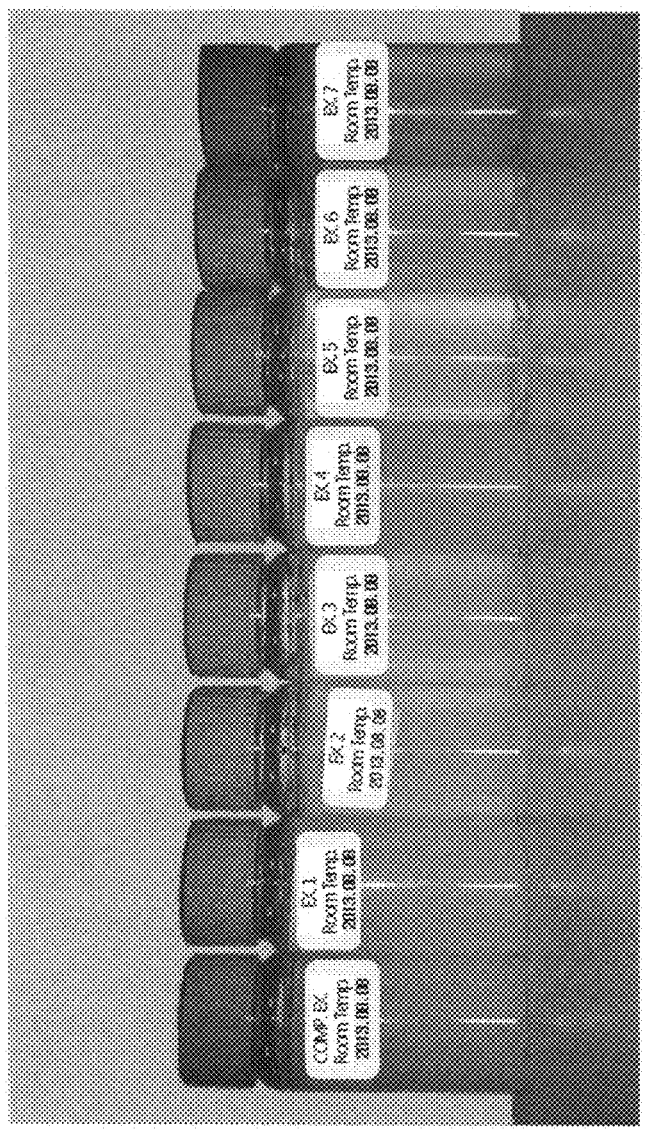
FIG. 1 shows the images taken by observing the appearance of each of the nanoemulsion formulations according to some embodiments of the present disclosure and the nanoemulsion according to Comparative Example (when viewed from the left side, Comparative Example 1, Example 1, Example 2, Example 3, Example 4, Example 5, Example 6 and Example 7).

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein.

Example 1: Preparation of Comparative Example and Examples

To stabilize intercellular lipid ingredients, nanoemulsion formulations are prepared by using the following compositions. Particularly, phase A is warmed and dissolved at 70-80° C. and introduced to phase C at room temperature. Herein, phase C is agitated constantly. Then, phase B warmed to room temperature or 40° C. is introduced gradually to phase C under agitation, and the resultant mixture is cooled and filtered to obtain each of the formulations. In Table 1, HCO (hydrogenated castor oil)-40, OD (octyldodeceth)-16 and Choleth-20 are non-ionic surfactants, and hydrogenated lecithin is phospholipid, and DPG and 1,3-PG are polyols.

Comparative Example 1 includes no surfactant in part A and part B, while Examples 1-4 include one type of surfactant in part A and part B, and Examples 5-7 include two types of surfactants (phospholipid and non-ionic surfactant). The formulation including one type of surfactant in part A and part B is prepared to determine whether or not a surfactant alone inhibits mass transfer at the interface to provide a stable nanoemulsion. However, in this case, it can be seen that the formulation causes degradation of stability at high temperature and under refrigeration after the test. Then, after carrying out additional tests, it is shown that a combination of phospholipid with a non-ionic surfactant provides improved stability at high temperature and during thawing after storage under refrigeration. Particularly, when using a Choleth type surfactant (particularly Choleth-15, 20), stability is improved significantly. It is thought that this is because a Choleth type surfactant having a structure similar to the structure of cholesterol contributes to formation of a more stable structure. In fact, when using no Choleth type surfactant or using a HCO type or OD type surfactant, the nanoemulsion causes degradation of stability (see, Test Example 1).

Test Example 1: Determination of Formulation Stability of Nanoemulsion

The stable formulations including intercellular lipid ingredients according to Examples and a formulation according to Comparative Example are subjected to a stability test at 50° C., at room temperature and under the condition of storage under cooling. To determine the stability of a formulation, each of Examples and Comparative Example is stored in a transparent container in a thermostat at 50° C., at room temperature and under cooling, and the stability is evaluated by the naked eyes at a predetermined time interval. In addition, during the test of formulation stability, the stability in a thermostat under refrigeration is determined by storing a formulation in a refrigeration thermostat for 3 days so that it is frozen completely and observing the suspension or precipitation in the formulation at room temperature, unlike the above-mentioned test method.

TABLE 1

| | | COMP. Ex. 1 | Ex. 1 | Ex. 2 | Ex. 3 | Ex. 4 | Ex. 5 | Ex. 6 | Ex. 7 |
|---|---|---|---|---|---|---|---|---|---|
| A | Ceramide | 0.1 | 0.1 | 0.1 | 0.1 | 0.1 | 0.1 | 0.1 | 0.1 |
| | Cholesterol | 0.1 | 0.1 | 0.1 | 0.1 | 0.1 | 0.1 | 0.1 | 0.1 |
| | HCO-40 | — | 0.2 | — | — | — | 0.2 | — | — |
| | OD-16 | — | — | 0.2 | — | — | — | 0.2 | — |
| | Choleth-20 | — | — | — | 0.2 | — | — | — | 0.2 |
| | Hydrogenated lecithin | — | — | — | — | 0.2 | 0.2 | 0.2 | 0.2 |
| | DPG | 5 | 5 | 5 | 5 | 5 | 5 | 5 | 5 |
| B | Alcohol | 5 | 5 | 5 | 5 | 5 | 5 | 5 | 5 |
| | Perfume | 0.05 | 0.05 | 0.05 | 0.05 | 0.05 | 0.05 | 0.05 | 0.05 |
| | HCO-40 | — | 0.1 | — | — | — | 0.1 | — | — |
| | OD-16 | — | — | 0.1 | — | — | — | 0.1 | — |
| | Choleth-20 | — | — | — | 0.1 | — | — | — | 0.1 |
| | Hydrogenated lecithin | — | — | — | — | 0.1 | — | — | — |
| C | Water | Balance | Balance | Balance | Balance | Balance | Balance | Balance | Balance |
| | 1,3-BG | 5 | 5 | 5 | 5 | 5 | 5 | 5 | 5 |

TABLE 2

| Test Item | | Comp. Ex. | Ex. 1 | Ex. 2 | Ex. 3 | Ex. 4 | Ex. 5 | Ex. 6 | Ex. 7 |
|---|---|---|---|---|---|---|---|---|---|
| Cooling | 1 week | X | ○ | ○ | ○ | ○ | ○ | ○ | ○ |
| | 2 weeks | X | ○ | ○ | ○ | ○ | ○ | ○ | ○ |
| | 4 weeks | X | Δ | Δ | Δ | Δ | ○ | ○ | ○ |
| Room temperature | 1 week | X | ○ | ○ | ○ | ○ | ○ | ○ | ○ |
| | 2 weeks | X | ○ | ○ | ○ | ○ | ○ | ○ | ○ |
| | 4 weeks | X | Δ | Δ | Δ | Δ | Δ | ○ | ○ |
| 50° C. | 1 week | X | Δ | Δ | Δ | X | ○ | ○ | ○ |
| | 2 weeks | X | X | X | X | X | Δ | Δ | ○ |
| | 4 weeks | X | X | X | X | X | X | X | ○ |
| Refrigeration | Run 1 | X | X | X | Δ | X | Δ | Δ | ○ |
| | Run 2 | X | X | X | X | X | X | X | ○ |
| | Run 3 | X | X | X | X | X | X | X | ○ |

○: good,
Δ: different from the initial time,
X: suspension or precipitation

After the test, Comparative Example using no surfactant causes a significant problem in stability, including suspension or precipitation under all tested conditions, as shown in Table 2. When using one type of surfactant in Examples 1-4, stability is degraded at high temperature and under refrigeration. Although Examples 5 and 6 using two types of surfactants show slight improvement of stability at high temperature, they cause precipitation in Run 2 during the thawing after refrigeration and show degradation of formulation stability. On the contrary, Example 7 shows a stable formulation under all tested thermostat storage conditions.

Test Example 2: Skin Safety Test of Nanoemulsion

Each of the formulations according to Comparative Example and Example 7 is evaluated for a skin irritation degree when applied to ten male and female adults not suffering from skin diseases as subjects. First, 20 μL of each sample is applied to the forearm of each subject. Next, the test site is sealed and is allowed to be covered with a patch for 24 hours. After removing the patch, the reaction on the skin after 30 minutes and 24 hours is examined based on the terminology suggested in the CTFA (Cosmetic, Toiletry and Fragrance Association) Guideline. The evaluation criteria are as follows. The grades obtained from the subjects according to the evaluation criteria are averaged, and then evaluated as low irritative (average<1), slightly irritative (average<3), moderately irritative (average<5) and highly irritative (average 5).

TABLE 3

| Test Item | Comp. Ex. | Ex. 7 |
|---|---|---|
| Skin Irritation Index (PII) | 0.21 | 0.24 |

It can be seen that the nanoemulsions including intercellular lipid ingredients according to Comparative Example and Example 7 show a low irritation degree less than 1 and thus are applicable to commercial products.

Figure 2:
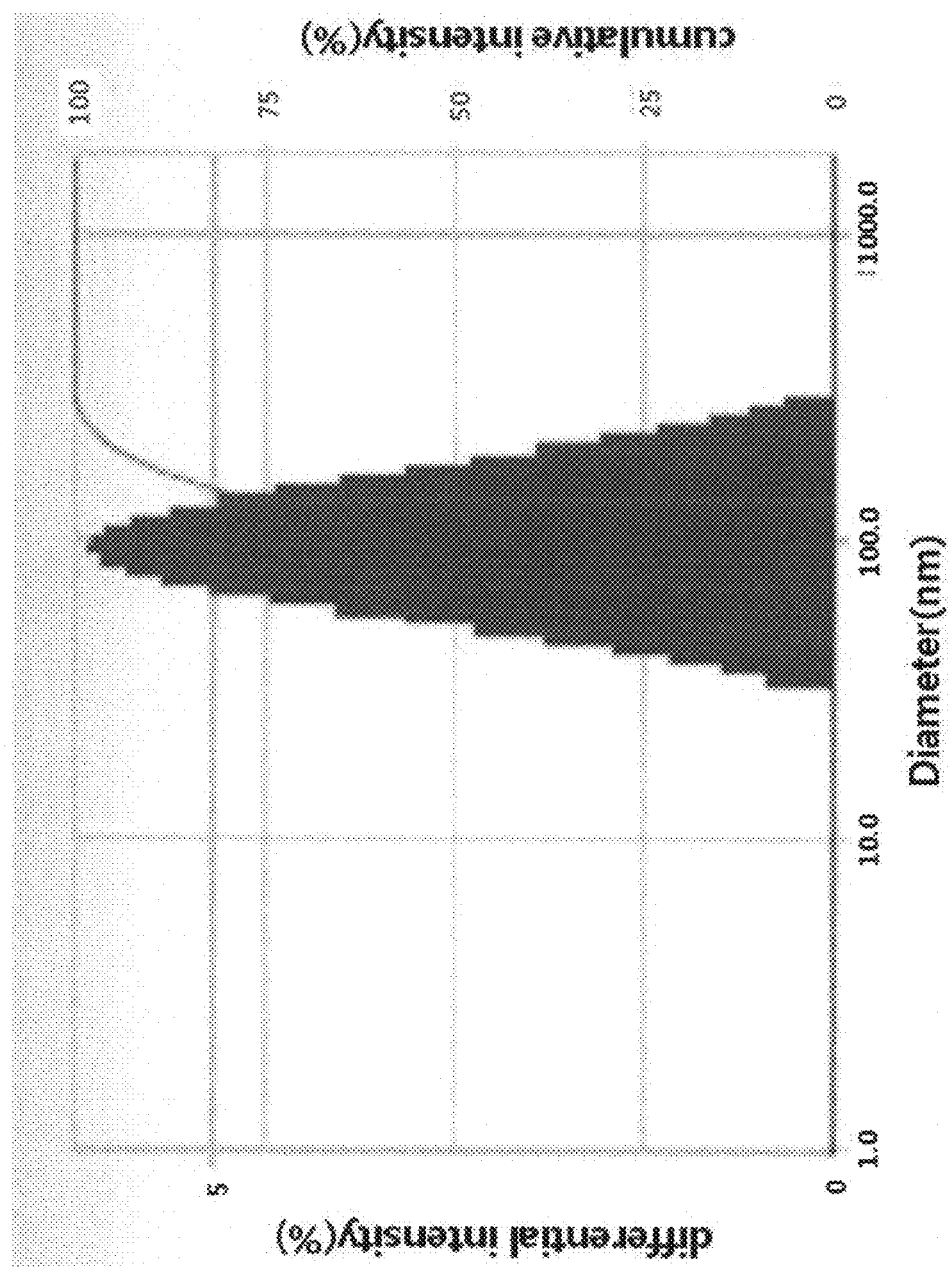
FIG. 2 shows the results of the particle size distribution of the stable nanoemulsion obtained by the method disclosed herein, as determined by using a dynamic light scattering (DLS) system.
Figure 3:
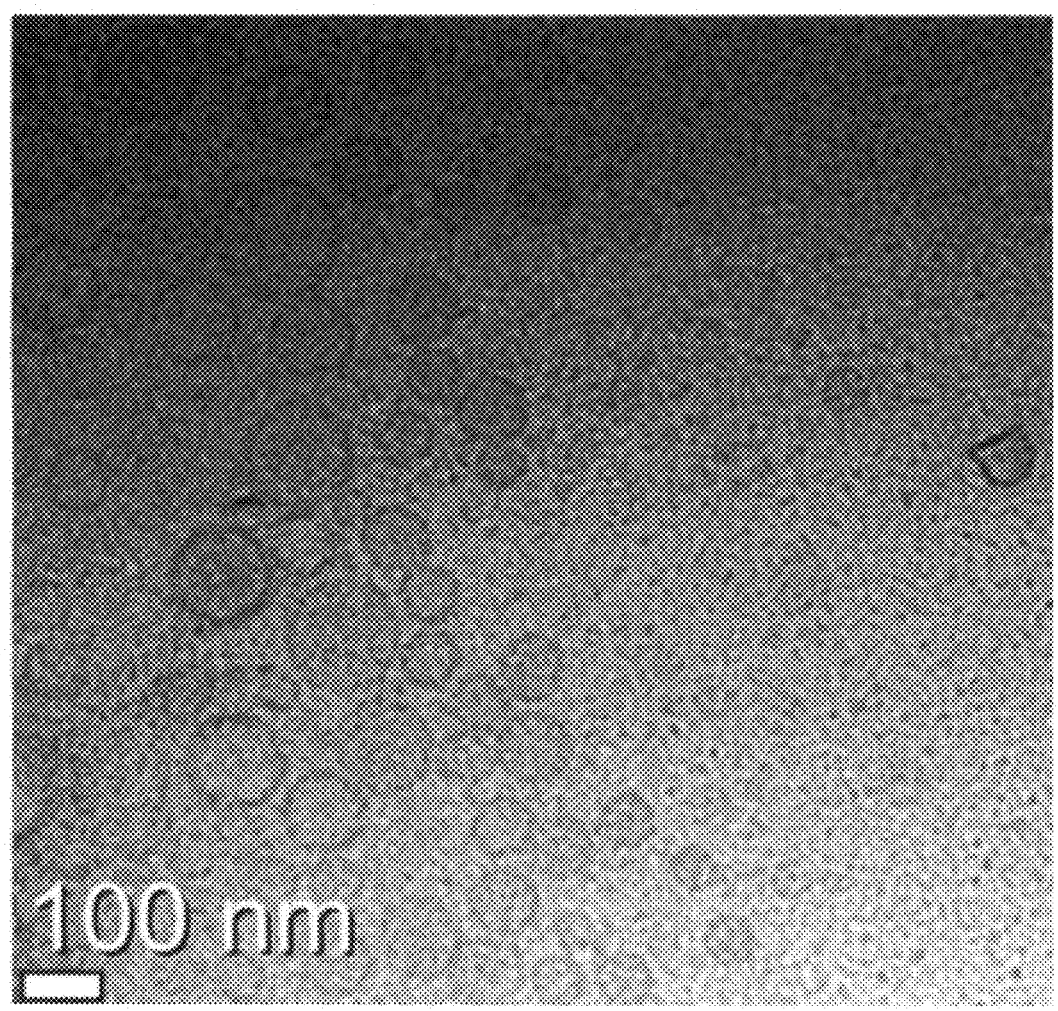
FIG. 3 shows the stable nanoemulsion obtained by the method disclosed herein, when observed by cryo-transmission electron microscopy (TEM).

Test Example 3: Determination of Particle Size and Observation of Properties of Nanoemulsion The stable formulation including intercellular lipid ingredients is determined for particle size distribution and properties by using dynamic light scattering (DLS) and cryo-transmission electron microscopy (Cryo-TEM). As shown in FIG. 2, Example 7 shows a particle size distribution corresponding to about 109 nm based on intensity. In addition, as shown in FIG. 3, it can be seen that Example 7 includes uniform circular nanoparticles having a size of about 100 nm.

The invention claimed is:

1. A method for preparing a nanoemulsion, comprising the steps of:
   a) mixing, warming and dissolving a ceramide or derivative thereof, cholesterol, first non-ionic surfactant, and a polyol to obtain an oil phase part (A);
   b) dissolving a perfume ingredient and second non-ionic surfactant into an alcohol to obtain a perfume part (B);
   c) dispersing or dissolving a polyol and water-soluble active ingredient into water to obtain an aqueous phase part (C);
   d) adding the oil phase part (A) to the aqueous phase part (C) and further adding the perfume part (B) to the aqueous phase part (C), followed by agitation, to obtain a reaction mixture; and
   e) filtering the reaction mixture of step d) through a filtering paper or a filtering cloth,
   wherein the first non-ionic surfactant or the second non-ionic surfactant is a mixture of phospholipid with hydrogenated castor oil, octyldodeceth, or Choleth.

2. The method for preparing a nanoemulsion according to claim 1, wherein the polyol used in step a) and the polyol used in step c) is at least one selected from the group consisting of propylene glycol, dipropylene glycol, 1,3-butylene glycol, pentylene glycol, and 1,2-hexanediol.

3. The method for preparing a nanoemulsion according to claim 1, wherein the first non-ionic surfactant is identical to the second non-ionic surfactant.

4. The method for preparing a nanoemulsion according to claim 1, wherein the perfume ingredient is oil used as perfume, perfume or a combination mixture thereof.

* * * * *